(12) United States Patent  (10) Patent No.: US 7,922,733 B2
Borghi  (45) Date of Patent: Apr. 12, 2011

(54) DEVICE FOR END-TO-SIDE ANASTOMOSIS

(75) Inventor: Enzo Borghi, Budrio (IT)

(73) Assignee: Newman Medical KFT, Budapest (HU)

( * ) Notice: Subject to any disclaimer, the term of this patent is extended or adjusted under 35 U.S.C. 154(b) by 683 days.

(21) Appl. No.: 11/885,348

(22) PCT Filed: Mar. 3, 2006

(86) PCT No.: PCT/IB2006/000462
§ 371 (c)(1),
(2), (4) Date: Aug. 30, 2007

(87) PCT Pub. No.: WO2006/092724
PCT Pub. Date: Sep. 8, 2006

(65) Prior Publication Data
US 2008/0195124 A1  Aug. 14, 2008

(30) Foreign Application Priority Data
Mar. 4, 2005  (IT) .............................. B02005A0120

(51) Int. Cl.
A61B 17/08 (2006.01)
(52) U.S. Cl. ...................................................... 606/153
(58) Field of Classification Search .................. 606/151, 606/153–156; 623/1.11, 1.23, 1.35, 1.36; 604/8–10
See application file for complete search history.

(56) References Cited

U.S. PATENT DOCUMENTS

| 4,822,341 | A | * | 4/1989 | Colone ......................... 604/175 |
| 5,893,886 | A |   | 4/1999 | Zegdi et al. |
| 6,007,576 | A | * | 12/1999 | McClellan ................. 623/23.64 |
| 6,254,618 | B1 |  | 7/2001 | Dakov |
| 6,395,015 | B1 |  | 5/2002 | Borst et al. |
| 6,485,513 | B1 |  | 11/2002 | Fan |
| 7,182,771 | B1 |  | 2/2007 | Houser et al. |
| 2004/0133221 | A1 | | 7/2004 | Sancoff et al. |
| 2005/0149075 | A1 | | 7/2005 | Borghi et al. |

FOREIGN PATENT DOCUMENTS

| DE | 102 05 997 | 9/2003 |
| EP | 0 895 753 | 2/1999 |
| FR | 1 518 083 | 2/1968 |
| WO | WO 01/41623 | 6/2001 |
| WO | WO 03/005698 | 1/2003 |

OTHER PUBLICATIONS

International Search Report for International Application No. PCT/IB2006/000462.

* cited by examiner

Primary Examiner — (Jackie) Tan-Uyen T Ho
Assistant Examiner — Gregory Anderson
(74) Attorney, Agent, or Firm — Fay Sharpe LLP

(57) ABSTRACT

A device for end-to-side anastomosis of body ducts comprising a coupling (2) which can be positioned on a side wall (3a) of a first duct (3) and connectable to a second duct (4) in order to create a fluid communication between the first (3) and second duct (4), and means of restraint (5) to firmly and preferably removably attach the coupling (2) to said first duct (3). The device (1) also comprises at least one membrane (6) removably positioned between the coupling (2) and side wall (3a) of the first duct (3) to prevent or allow the fluid communication between the first (3) and the second duct (4).

18 Claims, 13 Drawing Sheets

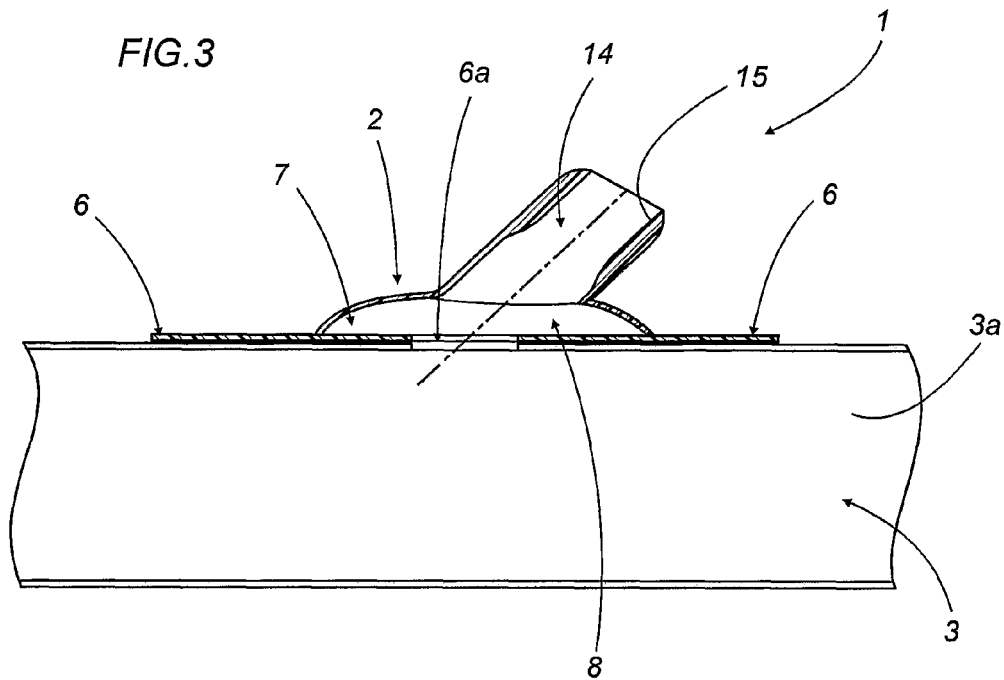
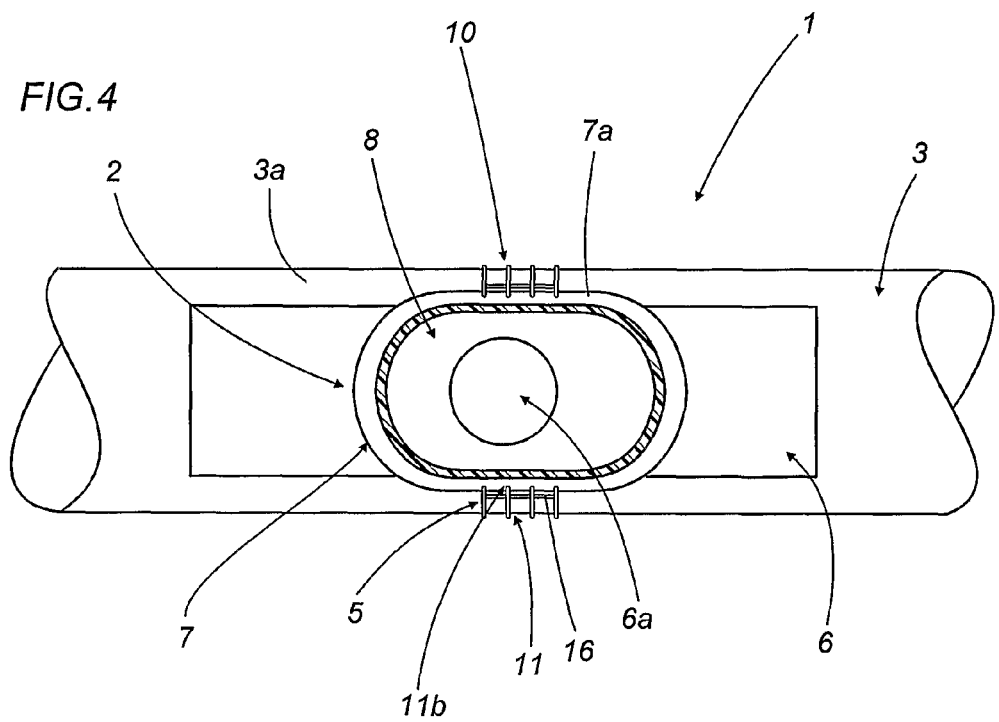

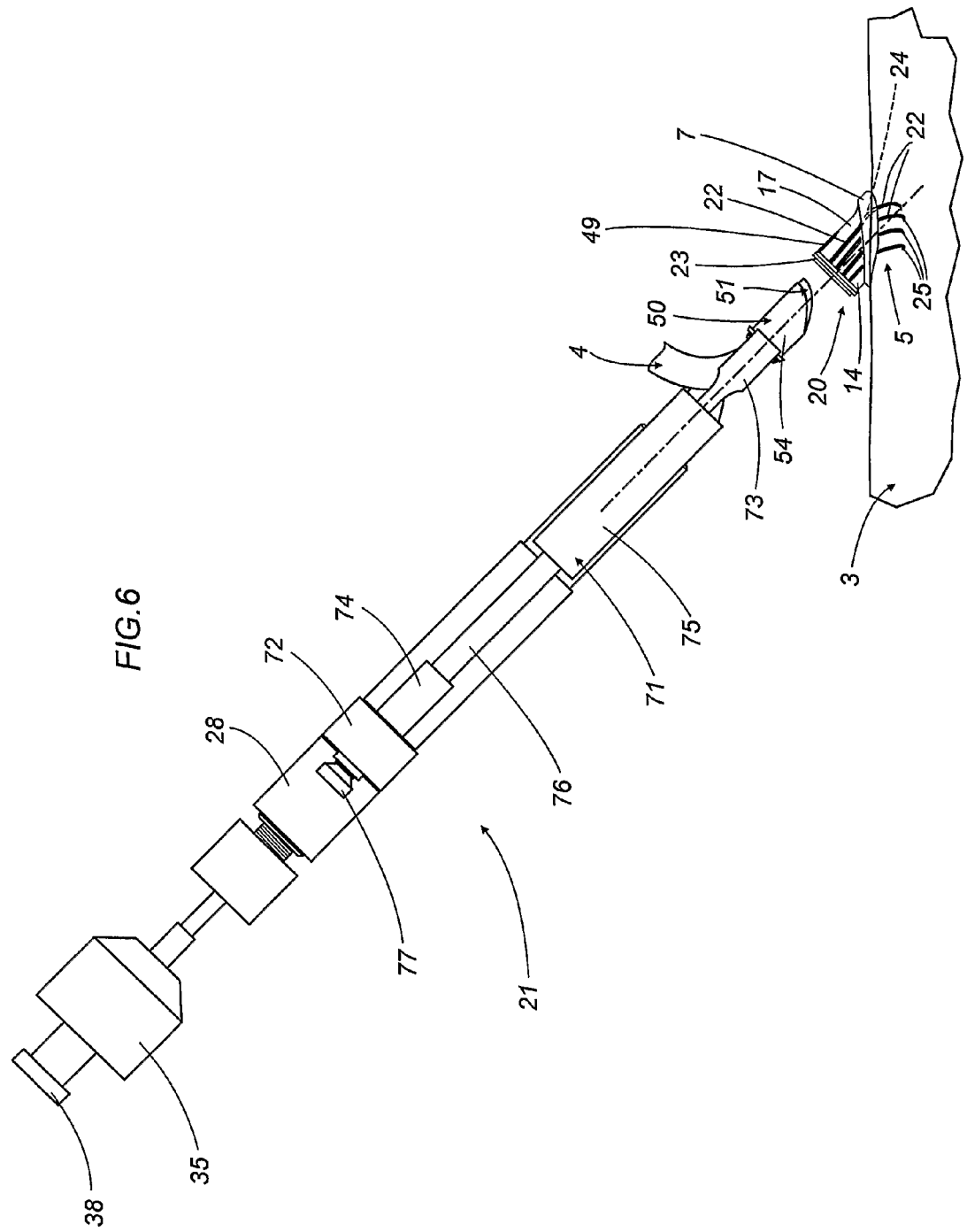

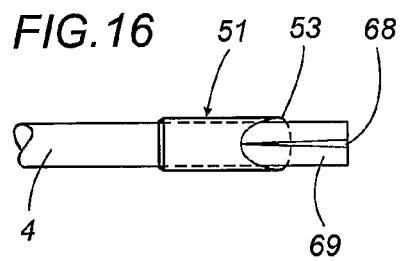
FIG.16
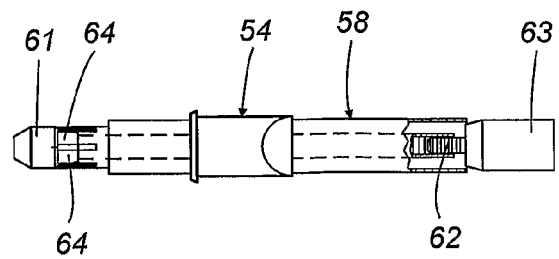
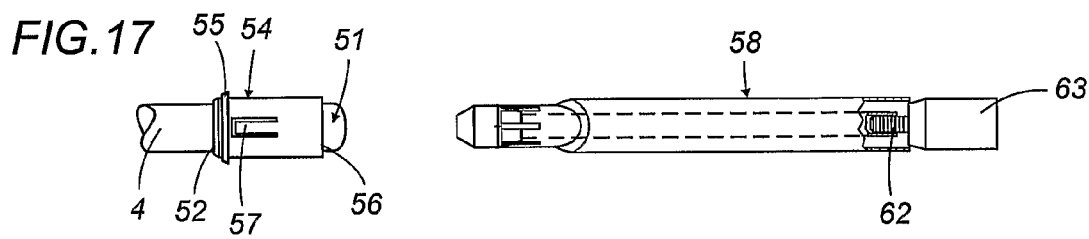
FIG.17
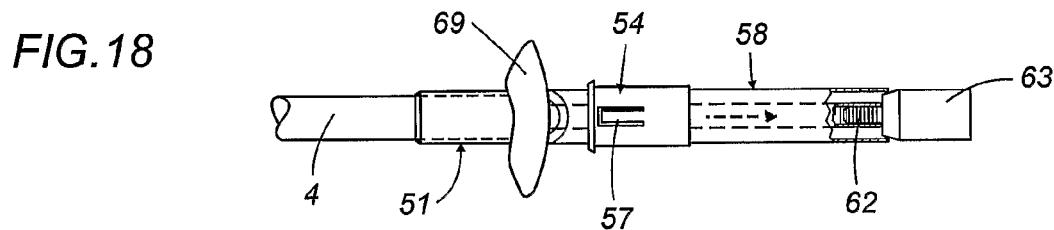
FIG.18
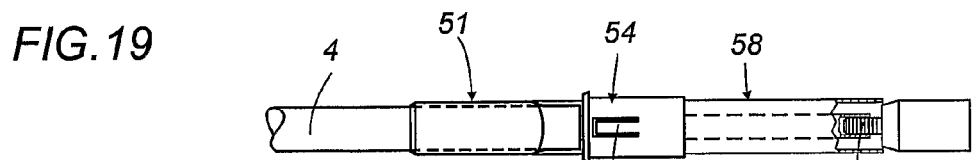
FIG.19
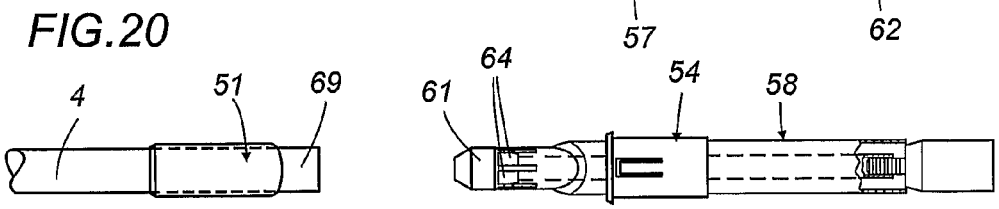
FIG.20
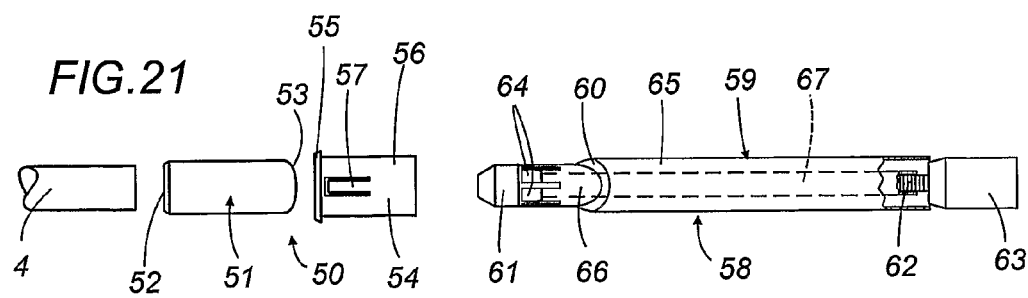
FIG.21

DEVICE FOR END-TO-SIDE ANASTOMOSIS

TECHNICAL FIELD

This invention relates to a device for an end-to-side anastomosis.

In surgery, the term anastomosis is used to mean a connection made between two hollow structures, such as for example blood vessels, lymph vessels, prostheses ducts and other ducts.

In particular, an end-to-side anastomosis is a connection between an end or head portion of a vessel with a portion of side wall of the same vessel or another vessel.

BACKGROUND ART

A first known type of anastomosis foresees the use of suture thread for sewing and thus connecting the free ends of two blood or lymph vessels. Before proceeding with the suturing, it is obviously necessary to prepare the two blood vessels so that they present free ends, for example by cutting the vessels.

A second known type of anastomosis foresees that, to connect two blood or lymph vessels, they are evaginated by means of appropriate mechanical clamping devices and then joined by their inner walls. In this case too it is necessary to prepare the blood vessels so that their ends are free.

A third known type of anastomosis does not foresee direct contact between the two blood or lymph vessels to be joined, but uses prosthetic ducts, generally made from metal, to restore the continuity of the blood vessel or to create a diversion from one blood vessel to another.

The Applicant has found that the prior art devices for end-to-side anastomosis can be improved from various points of view.

Suture anastomosis, in fact, produces a more or less accentuated scar in the vessel in question, not perfectly restoring the original continuity of the vessel.

In addition, suturing involves the repeated perforation of the inner wall of the vessel, causing considerable trauma and hemorrhaging of the vessel. The hemorrhage caused by the suture is even more accentuated by the fact that the vessels to be anastomosed must necessarily be cut in order to have respective free ends.

Suturing also causes an at least partial slipping of the various layers that make up the anastomosed vessel. Blood vessels, like lymph vessels are in fact made up of several coaxial and overlapping layers of organic material.

Finally, precisely because of the essential difficulty of the suturing operation of two blood or lymph vessels, the suture anastomosis must be carried out by highly skilled surgeons.

Mechanical anastomosis by eversion, while being easier to perform than suture anastomosis, is also unable to restore the original continuity of the vessel.

Eversion of the vessel flaps can also cause the ends to break, particularly if the diameter of the vessels is greater than 3 mm or if they are affected by sclerosis.

Another complication, specific to blood vessels, is caused by the fact that the inside layers of the vessel ends, after being turned inside out and placed side by side, are no longer exposed to blood flow and therefore tend to atrophy and, in the most extreme cases, to become necrotic, causing pressure in the blood vessel which leads to narrowing.

Devices for end-to-side anastomosis which do not foresee direct contact between the two vessels being operated on present the drawback of involving direct contact between the metallic material of the prosthetic duct and the blood flow, which, as is known, can cause a risk of occlusion of the prosthetic duct by stenosis.

This drawback can be overcome by coating the metals used to manufacture the prosthesis with anti-stenosis substances which, however, do not always ensure against the subsequent formation of thrombi and the onset of acute thrombosis, exposing the patient to considerable risk.

In addition, apart from the known type of end-to-side anastomosis device used, an anastomosis operation always takes a considerable amount of time, exposing the patient to stress and other factors that can worsen his or her general physical condition.

Finally, in view of the highly invasive nature of known devices for end-to-side anastomosis, operations involving anastomosis are very often accompanied by abundant hemorrhage, sometimes requiring interruption of the circulation in the vessel being operated on.

DISCLOSURE OF THE INVENTION

In this context, the main technical aim of this invention is to propose a device for end-to-side anastomosis that does not present the drawbacks described above.

In particular, this invention aims to provide a device for end-to-side anastomosis that causes limited hemorrhaging during the graft operation.

An additional aim of this invention is to propose a device for end-to-side anastomosis that restores the original continuity of the anastomosed vessel.

Yet another aim of this invention is to provide a device for end-to-side anastomosis that can be positioned in a relatively short time.

A further aim of this invention is to provide a device for end-to-side anastomosis that can be easily positioned, offering extremely reduced learning times for this operating method.

These aims are substantially achieved by a device for end-to-side anastomosis comprising the technical features described in one or more of the attached claims.

BRIEF DESCRIPTION OF THE DRAWINGS

Additional features and advantages of this invention will become clear from the indicative, and thus not binding, description of a preferred but not exclusive embodiment of a device for end-to-side anastomosis, as shown in the accompanying drawings in which:

FIG. 3 is a cross-section of the device in FIG. 1 along the plane III-III;

FIG. 4 is a cross-section of the device in FIG. 1 along the plane IV-IV;

FIG. 6 shows a preferred embodiment of a device according to the invention, in side view;

FIGS. 16 to 21 show successive application steps of a prosthesis to an end connector;

DETAILED DESCRIPTION OF THE PREFERRED EMBODIMENTS OF THE INVENTION

Figure 1:
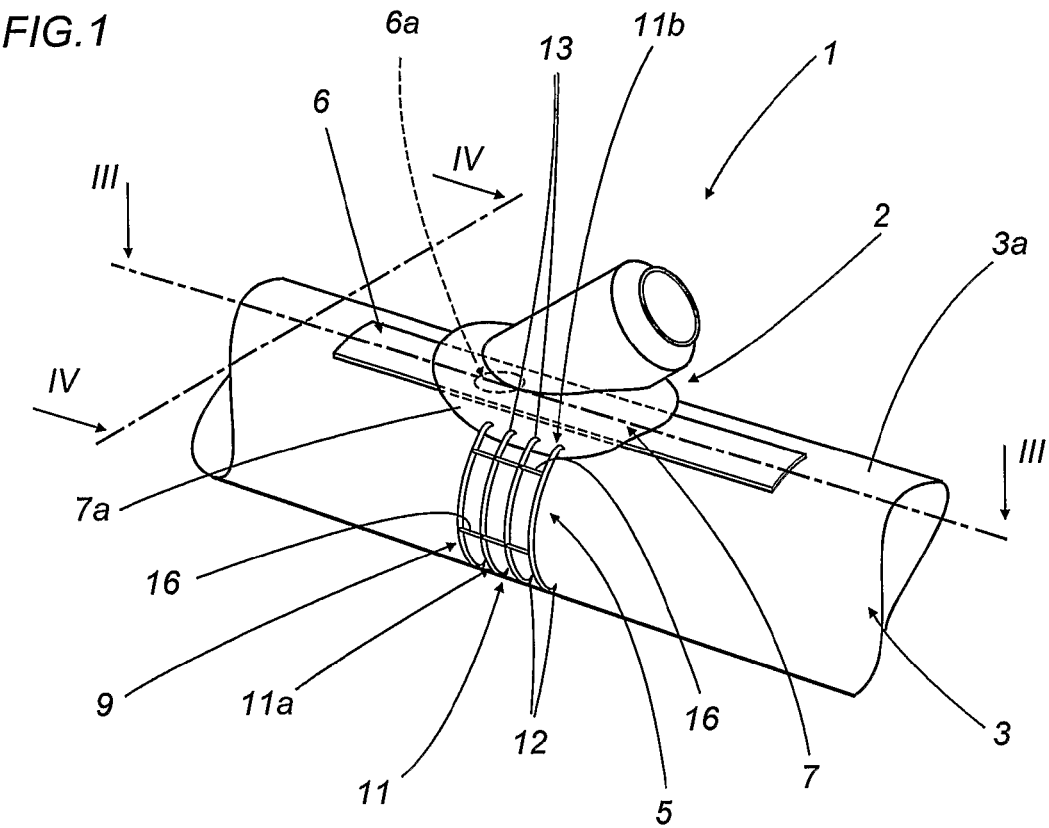
FIG. 1 is a prospective view of a device for end-to-side anastomosis according to this invention in a first working position.

With reference to the accompanying FIGS. 1 to 5, the number 1 indicates a device for end-to-side anastomosis according to this invention.

The device 1 comprises a coupling 2 that can be positioned on a wall 3a of a first duct 3. The coupling 2 can be connected to a second duct 4 so that the first 3 and second duct 4 can be placed in fluid communication with each other. The ducts 3, 4 can be blood vessels, lymph vessels or prosthetic ducts as necessary, that is to say according to the type of operation to be carried out. The device 1 also comprises means of restraint 5 for firmly and preferably removably attaching the coupling 2 to the first duct 3 and at least one membrane 6 removably positioned between the coupling 2 and the side wall 3a of the first duct 3, to prevent or allow fluid communication between the first 3 and the second 4 duct.

In particular, as can be seen in the accompanying figures, the coupling 2 comprises a saddle-shaped portion 7 at least partially overlapping the wall 3a of the first duct 3. The saddle-shaped portion 7 has an opening 8 (FIGS. 3 and 4) in order to place the first duct 3 in fluid communication with the second duct 4. The saddle-shaped portion 7 is the part of the coupling 2 counter-shaped, in the contact area, to the side wall 3a of the first duct 3, so that the coupling fits perfectly on top of the first duct 3. To increase the degree of adhesion and contact between the saddle-shaped portion 7 and the first duct 3, the saddle-shaped portion 7 is made from compliant material so that it adapts perfectly to the curvature of the side wall 3a of the first duct 3.

To attach the coupling 2 to the first duct 3, the device 1 comprises means of restraint 5.

According to the invention, these means of restraint 5 act with a clamping mechanism on the wall 3a of the duct, in order to guarantee a firm and balanced anchorage of the device.

In particular, in the embodiment shown in FIGS. 1 to 5, the means 5 comprise at least two elements 9, 10, preferably elastically deformable, which at least partially encircle the first duct 3. The two elements 9, 10 extend from the saddle-shaped portion 7 of the coupling 2 overlying the side wall 3a of the first duct 3. More specifically, the two elements 9, 10 extend from the edge 7a of the saddle-shaped portion 7 from opposite positions with respect to the opening 8.

Figure 2:
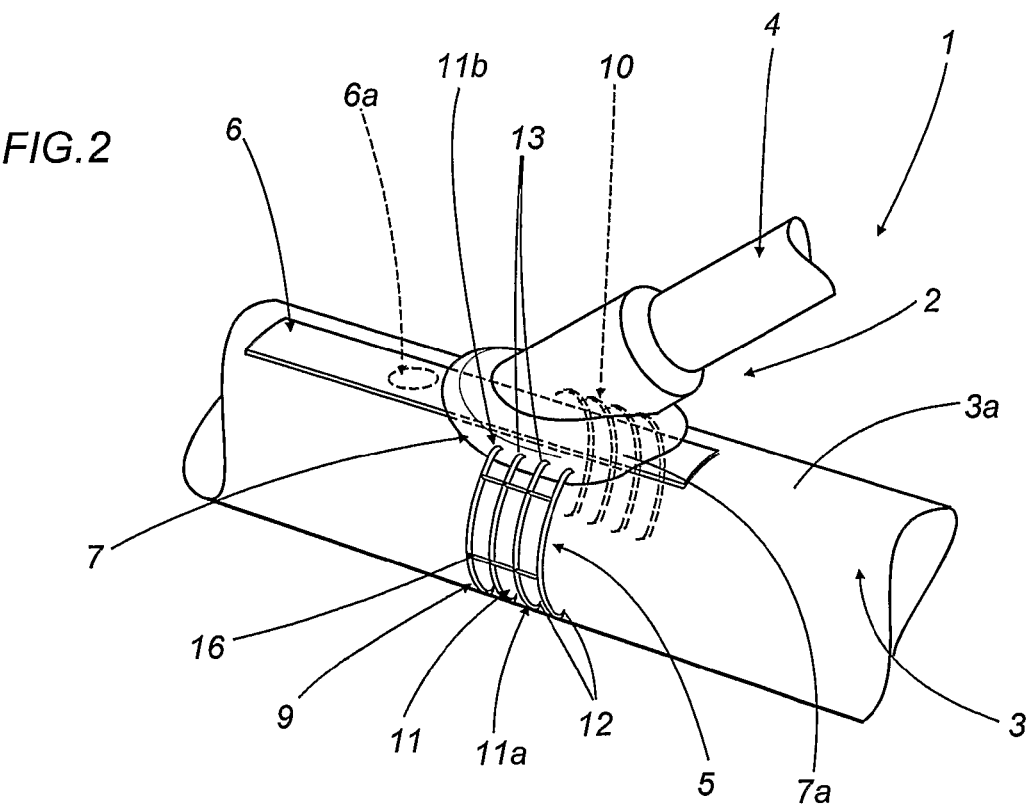
FIG. 2 is a prospective view of the device in FIG. 1 in a second working position.

Advantageously, each elastically deformable element 9, 10 comprises a fastener 11, which extends along the side wall 3a of the first duct 3. Each fastener 11 comprises at least one hook 12 for attaching it firmly to the side wall 3a of the first duct 3. In the preferred embodiment, as shown in FIGS. 1 and 2, there are four hooks 12 for each of the two fasteners 11, but the number may be different, for example six (see FIG. 5). Regardless of the number of hooks 12 present, which can vary according to the type of anastomosis to be fashioned and according to the cross-section of the duct to be anastomosed, each hook 12 advantageously only partially perforates the side wall 3a of the first duct 3, in order to firmly secure the fastener 11, and thus the coupling 2, to the first duct 3. In other words, to reduce the lesions to the duct to be anastomosed to a minimum, the hook 12 only perforates the surface tissue layers of the vessel to be anastomosed.

Each hook 12 is positioned at the end 11a of the fastener 11 distal from the edge 7a of the saddle-shaped portion 7.

The fastener 11 also presents a second end 11b, opposite the first 11a, attached to the coupling 2. In particular, the second end 11b is removably attached to the edge 7a of the saddle-shaped portion 7. The attachment between the fastener 11 and the edge 7a of the saddle-shaped portion 7 is achieved, in the preferred embodiment shown in FIGS. 1 and 2, by means of claws 13 which allow, if necessary, the fastener 11 to be detached from the saddle-shaped portion 7. It should be pointed out that the attachment between the fastener 11 and the saddle-shaped portion 7 can be achieved by any other means that allow the fastener 11 to be detached from the saddle-shaped portion 7. In fact, in a variation shown in FIG. 5, the attachment between the fastener 11 and the saddle-shaped portion 7 is achieved by engaging the end 11c of the fastener 11 in a housing 7b in the edge 7a of the saddle-shaped portion 7.

As far as materials are concerned, the fastener 11 is preferably made from biocompatible material.

In a preferred embodiment (shown in FIG. 1), the elements 9 of the fastener 11 also present one or more connecting bars 16 which reciprocally join the elements 9 and improve the stability of the attachment to the vessel 3.

The coupling 2 also comprises a conduit 14 that extends from around the opening 8 in the saddle-shaped portion 7 and away from the opening 8. The conduit 14 is connected to the saddle-shaped portion 7 and is in fluid communication with the opening 8.

The conduit 14 also forms an angle with the plane containing the opening 8, which, according to the application, is between 30° and 90°, preferably 30°, 35°, 45° or 90°.

At the opposite end to the saddle-shaped portion 7, the conduit 14 comprises a coupling portion 15 to connect the coupling 2 to the second duct 4.

In the embodiment shown in the accompanying figures, given as a non-binding example, the second duct 4 can consist of a prosthetic duct. In this case, the second duct 4 can be cut to size and prefitted with an end connector 15' to be connected to another coupling (not shown) which, in turn, can be grafted onto a blood vessel.

Advantageously, the connection between the coupling portion 15 of the conduit 14 and the second duct 4 is mechanical, in other words it is sufficient to insert the second duct 4 in the coupling portion 15 to achieve a firm restraint between the two elements.

Alternatively, the connection between the coupling portion 15 of the conduit 14 and the second duct 4 can be the snap-fit or bayonet type.

According to what is described, the coupling 2 is in fluid communication with the second duct 4 through the opening 8 and the conduit 14.

To achieve the aforesaid fluid communication between the coupling 2 and the first duct 3, it is necessary to intervene on the first duct 3. In fact, the saddle-shaped portion 7, and thus the opening 8, face onto the side wall 3a of the first duct 3. These operations will be described in detail below.

It is, in any case, necessary to point out that advantageously the membrane 6 obstructs the opening 8 in the saddle-shaped portion 7, preventing the passage of fluid between the ducts 3, 4. More specifically, by obstructing the opening 8, the membrane 6 cuts off the coupling 2 from the first duct 3 to allow the correct positioning of the coupling 2 on the first duct 3.

The membrane 6 can, also advantageously, be perforated in correspondence with the opening 8 so that the opening 8 is in fluid communication with the coupling 2, and, finally, the first duct 3 with the second duct 4.

When in use, in fact, the device 1 is applied according to the following procedure.

By means of its saddle-shaped portion 7, the coupling 2 is positioned on the side wall 3a of the first duct 3 to be anastomosed.

The membrane 6 is located between the saddle-shaped portion 7 and the side wall 3a of the duct 3, obstructing the opening 8 in the saddle-shaped portion 7 (FIG. 1).

The fasteners 11 encircle the side wall 3a of the first duct 3 and, by means of the hooks 12, hook onto the surface tissues of the side wall 3a of the duct 3.

It should be stressed that the restraint between the coupling 2 and the fasteners 11 can be established before (embodiments shown in FIGS. 1, 2 and 5) or after (embodiment shown in FIGS. 1 and 2) the hooks 12 have been attached to the side wall 3a of the duct 3.

At this point, the coupling 2 is in position on the duct 3 to be anastomosed, but fluid communication is not yet established between the duct 3 and the coupling 2, thus preventing any hemorrhage.

A knife with a cup-blade and a helix, or a hook-shaped needle, to withdraw the cut tissue (not shown), is inserted through the conduit 14, perforating the membrane 6 and the side wall of the underlying duct through the opening 8, creating the hole 6a.

When the knife is withdrawn through the conduit 14, the portion of cut tissue and the corresponding portion of membrane are removed by means of the helix, thus creating a fluid connection between the first duct 3 and the coupling 2 which, however, is not yet connected to the second duct 4.

Advantageously, to prevent any leakage of body fluid from the anastomosed duct 3, once the knife has been withdrawn the membrane 6 is moved (see FIG. 2) so that a portion that was not perforated obstructs the opening 8, interrupting the fluid connection between the first duct 3 and the coupling 2.

The conduit 14 is thus connected (as can be seen in FIG. 2) to the second duct 4 through the coupling portion 15, establishing a fluid connection between the coupling 2 and the second duct 4.

Advantageously, the membrane 6 is now completely removed (see for example FIG. 5), that is to say it is extracted from its position between the saddle-shaped portion 7 and the side wall 3a of the first duct 3, establishing fluid communication between the first duct 3 and the second duct 4 through the coupling 2.

With reference to FIGS. 6-23 a preferred embodiment is described of a device 20 according to the invention and an applicator 21 of the device to a duct or vessel 3.

In FIGS. 6-23, the same numerical references are used for the parts of the invention corresponding to those already described above.

In the device 20, the means of restraint 5 consist of a series of hooks 22 preferably made from elastic metal wire positioned at the two sides of the saddle 7 and the conduit 14.

Figure 7A:
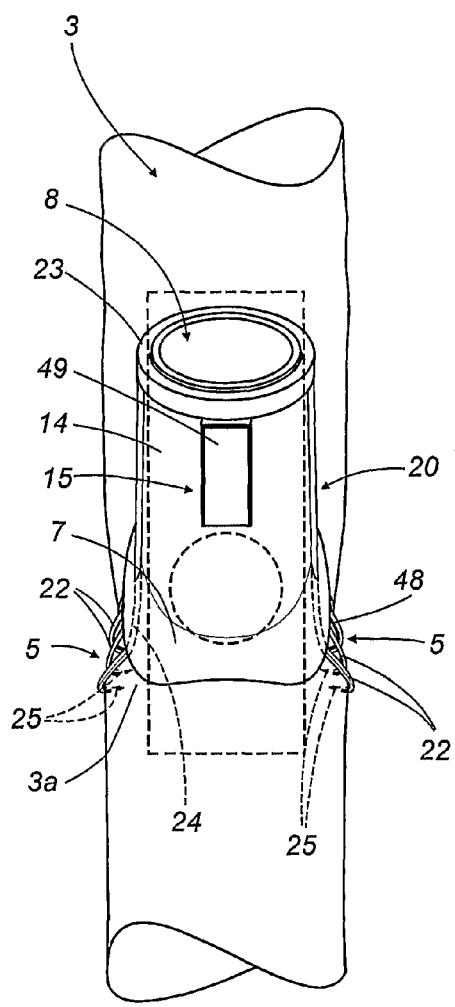
FIG. 7a is a view from above of the device in FIG. 6.
Figure 7B:
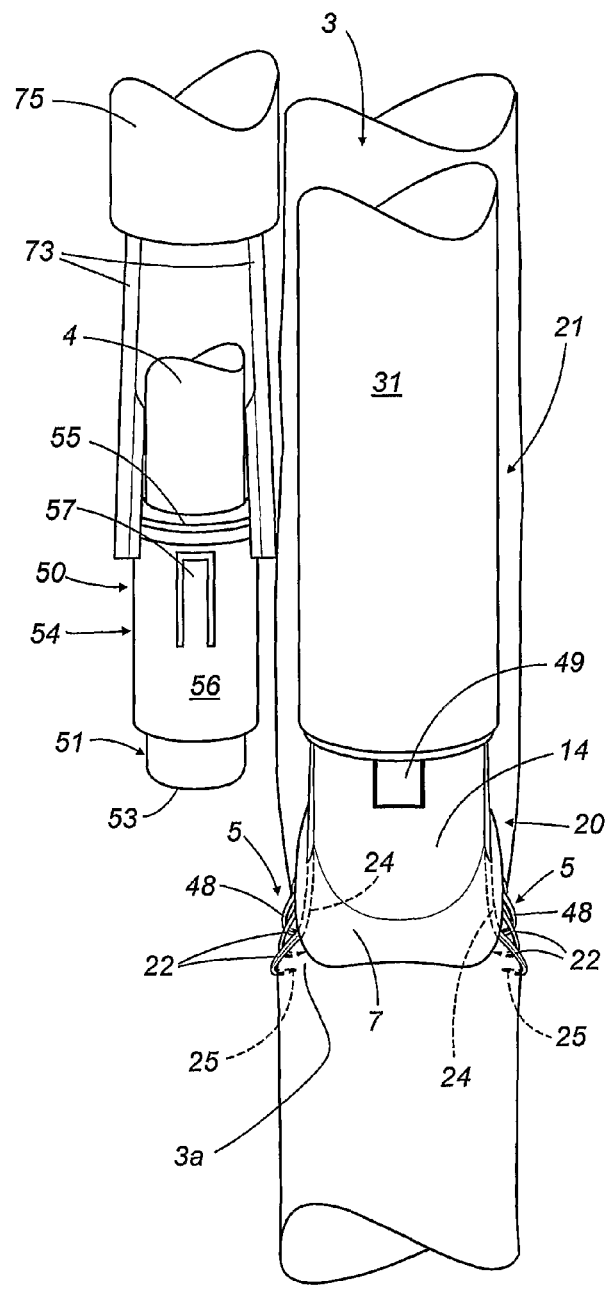
FIG. 7b is a view of the device in FIG. 7a with a schematised device applicator.

More specifically, the hooks 22 are connected at one end to a ring 23 sliding along the conduit 14 and pass through slits 24 cut in the sides of the saddle 7, protruding below it with a curve 48 and terminating with bent ends 25, normally open and designed to grip the wall 3a of the duct 3 in the closed configuration (FIGS. 7a, 7b).

With reference to FIGS. 8 to 15 an applicator 21 designed to apply a device 20 to a duct 3 is now described.

Figure 12A:
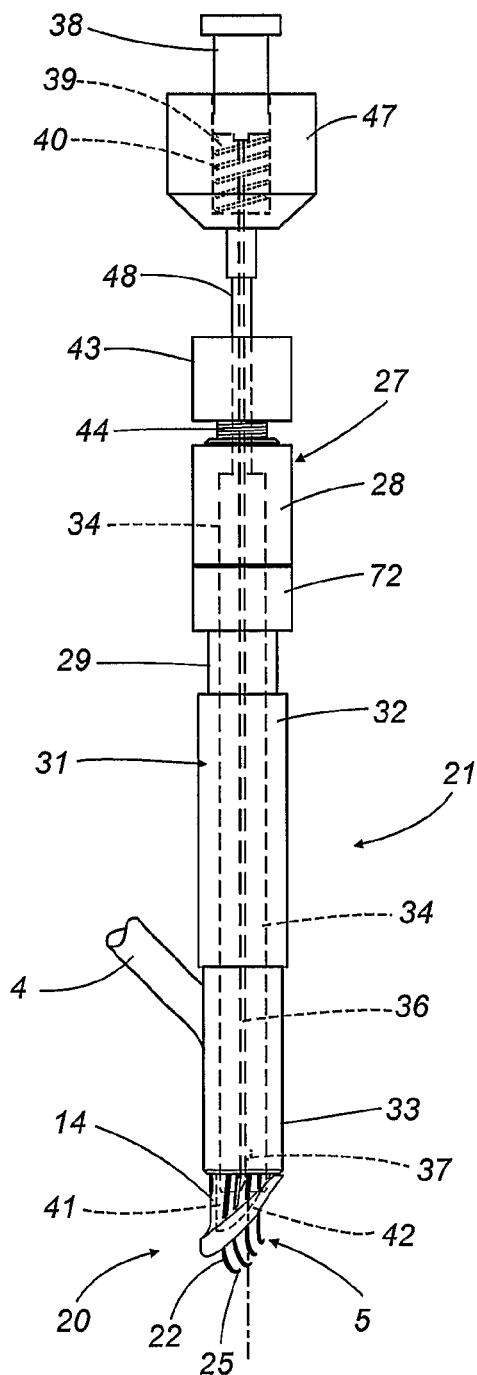
FIG. 12a is an assembly view of the applicator in FIG. 8 with a device according to FIGS. 6 and 7a,b fitted, with the inner components indicated by dashed lines.

With particular reference to FIG. 12a, the applicator 21 comprises:

a first tubular body 27 consisting of a grip portion 28 from which a portion with a smaller diameter 29 protrudes and ends with a crown of elastic metal segments 30 normally divergent and equipped with restraining teeth 45.

a cylindrical sleeve 31 sliding over the portion 29 and consisting in turn of a grip section 32 and a front portion with a smaller diameter 33;

a second tubular body 41, inside and coaxial to the body 27, equipped at the front with a stop ring 46 and a sloping end 42. The body 41 is also equipped at its rear end with threading 44 which engages with a nut screw 43 that can be turned by the operator so as to axially slide the body 41 with respect to the first tubular body 27;

a cup-shaped knife 34 with a front cutting end 35 positioned inside and coaxial to the body 41 with respect to which it can be rotated and slid axially by means of a knob 47 attached to the knife 34 by means of a smaller diameter cylinder 48;

a metal rod 36 equipped with an end hook 37 coaxial to the knife 34 with respect to which it can be slid by operating a pushbutton 38 inserted in and becoming flush with a cavity 39 in the knob 47 against the action of a compression spring 40.

Figure 12B:
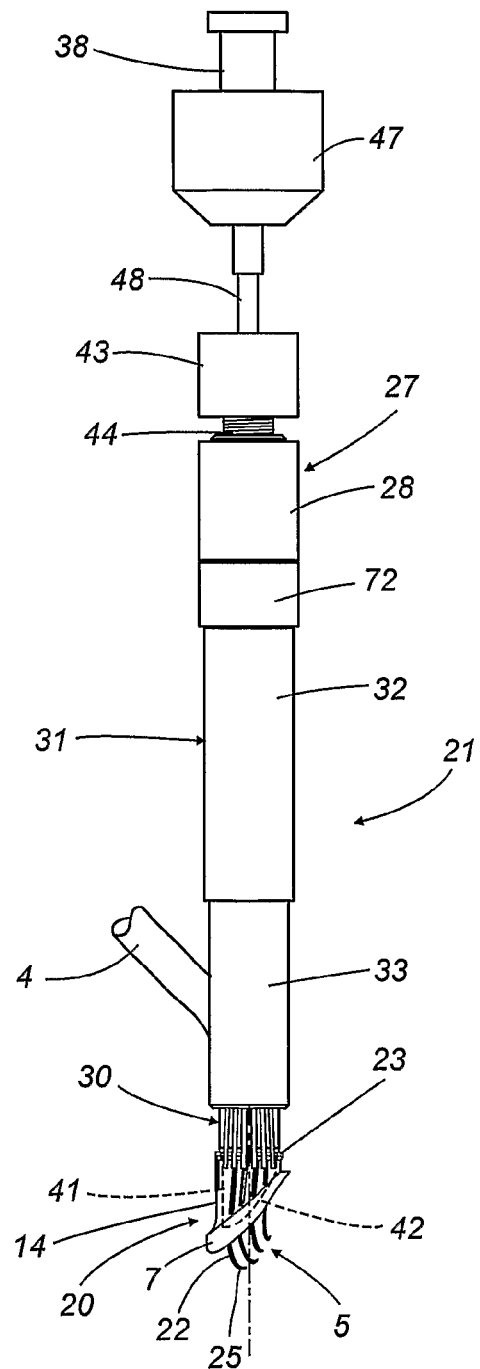
FIG. 12b is the applicator in FIG. 12a with a device inserted but not locked in the applicator.

With reference in particular to FIGS. 12a and 12b the following procedure is employed to fit a device 20 on an applicator 21.

The conduit 14 of the device 20 is fitted on the sloping end 42 of the tubular body 41 as far as the collar 46 so that the sloping end 42 of the cylinder 41 coincides with the opening 8 of the device.

In this configuration (FIG. 12b), the segments 30 are normally divergent and surround and protrude at the front of the ring 23 which slides on the conduit 14 of the device 20.

To block the device 20 in the applicator it is sufficient to slide the sleeve 31 forward, forcing the segments 30 to close and engage the ring 23 with the teeth 45 (FIG. 12a).

Figure 13:
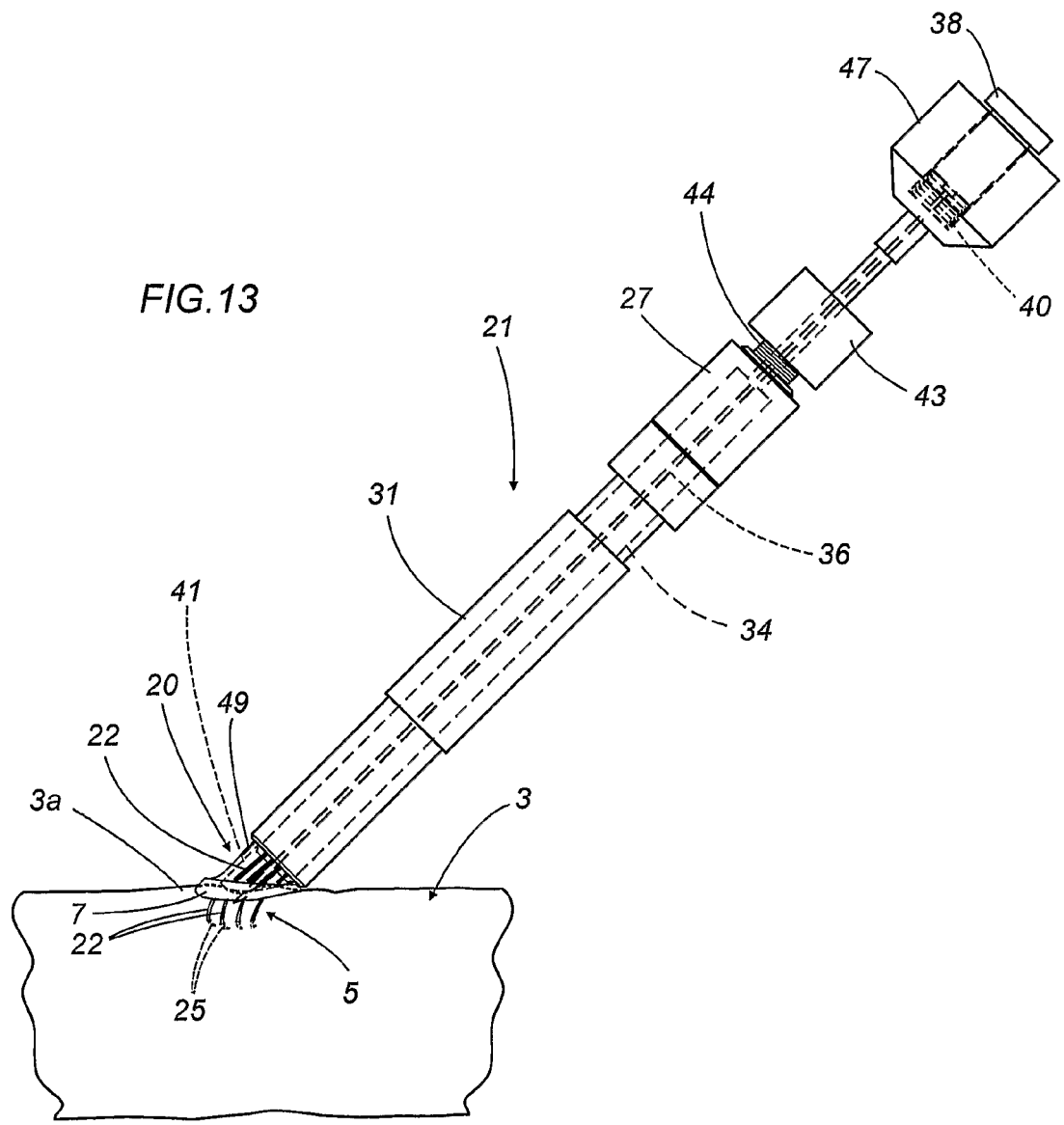
FIG. 13 is a side view of the assembly in FIG. 12a with the device applied to a duct or vessel.
Figure 14:
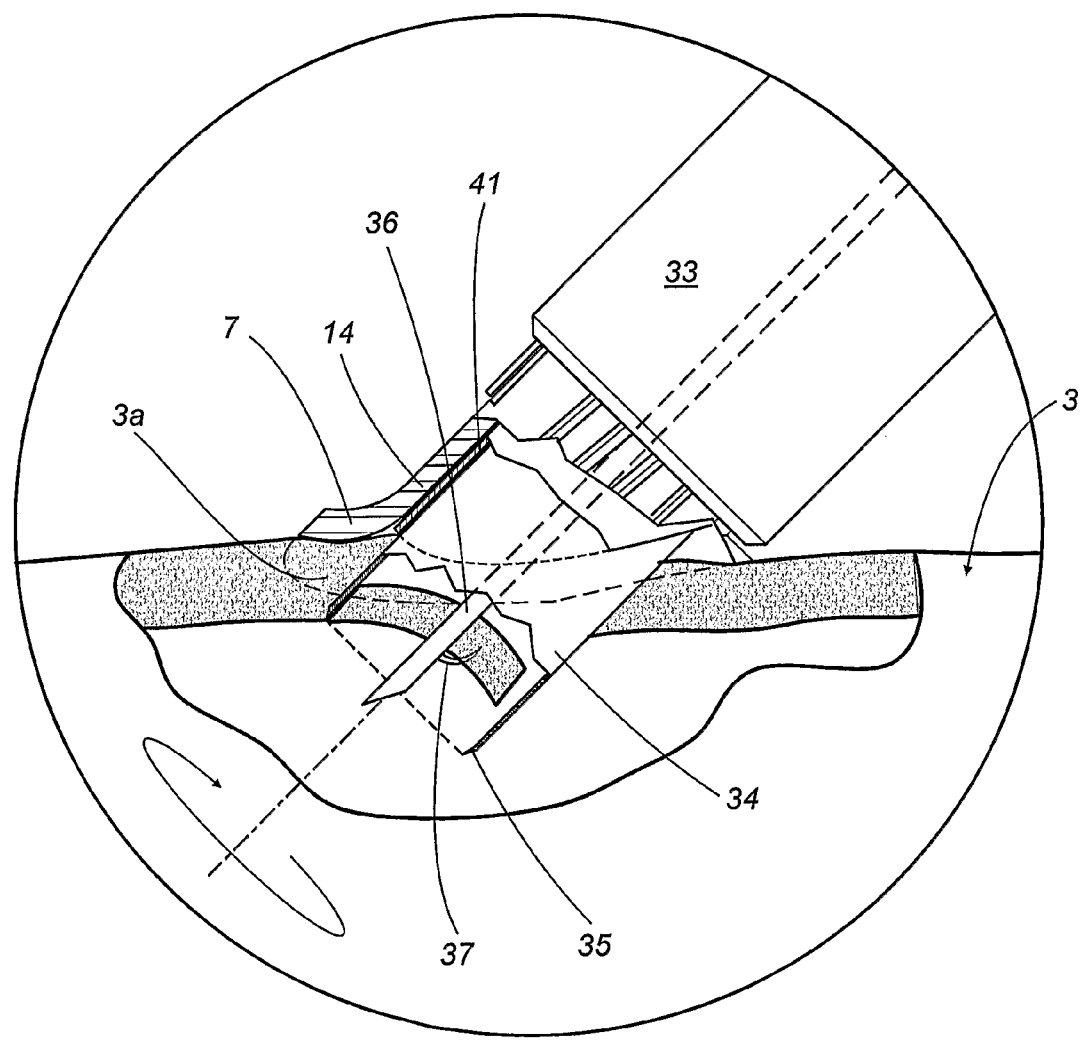
FIG. 14 is a detail in partial longitudinal cross-section of the assembly in FIG. 13 during application of the device to a blood vessel.
Figure 15:
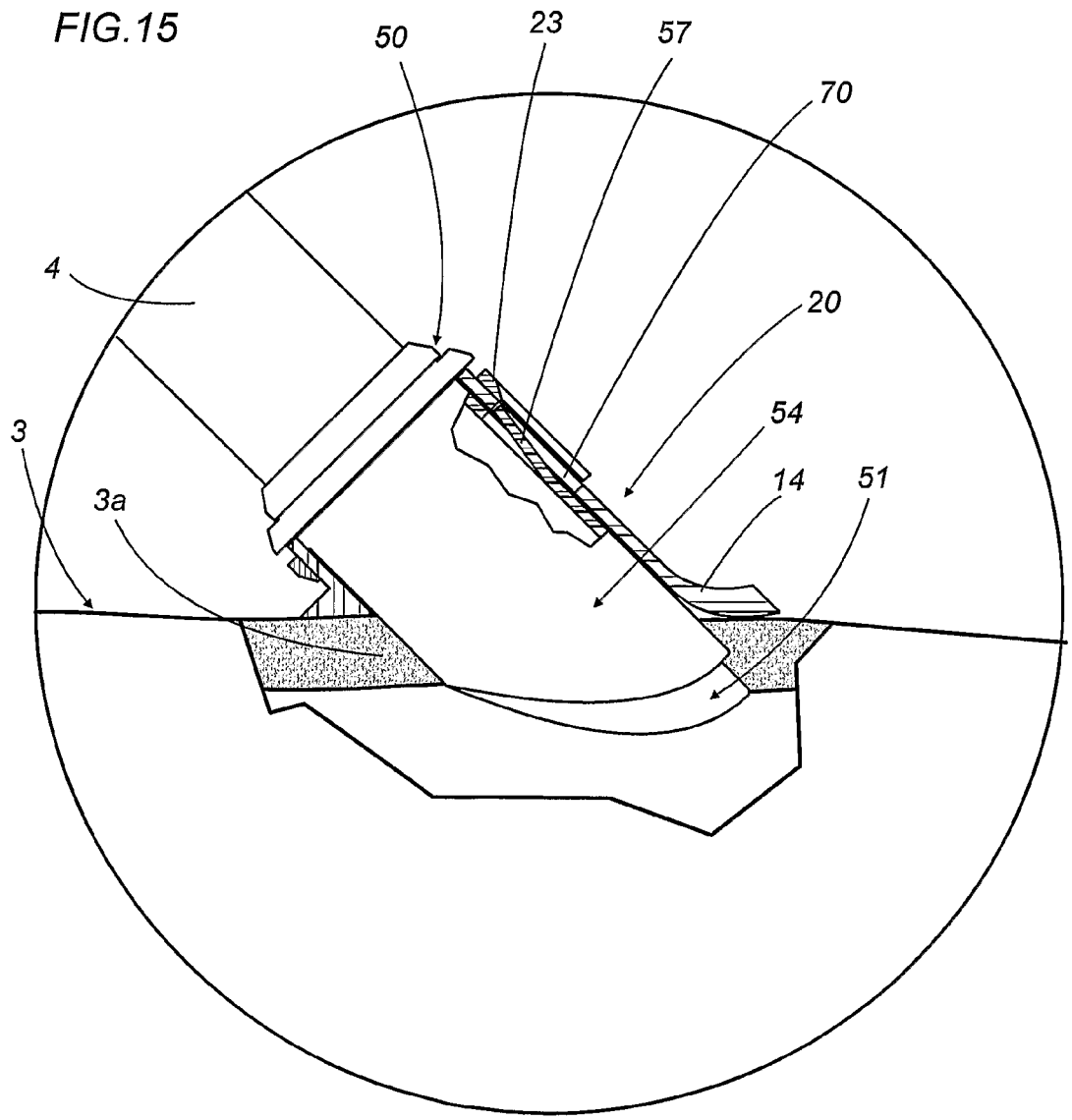
FIG. 15 is a side view in partial cross-section of the anastomosis device according to the invention applied to a duct or vessel and assembled with an end connector holding a side duct or prosthesis.
Figure 22:
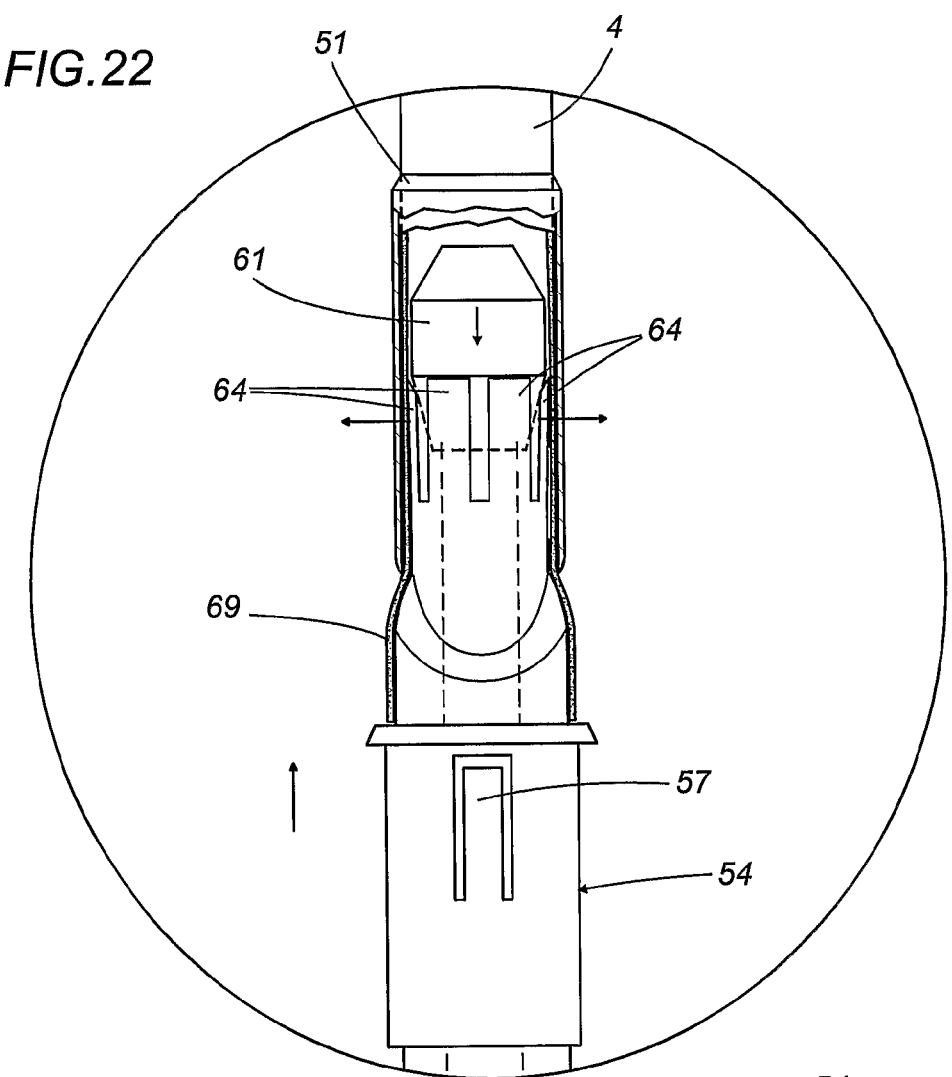
FIG. 22 shows a detail in longitudinal cross-section of an end connector, during application of a prosthesis by means of an expansion applicator.

With particular reference to FIGS. 13 to 15, to apply the device 20 fitted in the applicator 21 to a duct 3 the following procedure is adopted.

The ring 23 is in the advanced position on the conduit 14 and the curved ends 48 of the hooks are free so that the fastener ends 25 are in the normal open position, allowing the device 20 to be positioned on the wall 3a of a duct 3.

By turning the knob 43 the body 41 moves forward, pushing the collar 46 and the conduit 14 forward, while the ring 23, being held in position by the teeth 45 of the segments 30, slides in relation to the conduit 14 and causes the hooks 22 which slide in the slits 24 in the saddle 7 to withdraw.

Preferably, there is also a safety segment 49 (visible in FIG. 7a) which engages with the ring 23 when it is in the maximum withdrawn position, preventing it from spontaneously moving forward again.

Due to the withdrawal of the hooks 22, the curved part 48 of the metal wires forming the hooks 22 is forced to straighten by entering the slits 24, causing the ends 25 of the hooks 22 to close and grip the two sides of the wall 3a and partially perforate it (FIG. 7a, 7b) fixing the device 20 to the duct 3. With particular reference to FIG. 14 the incision of the duct 3 is shown in detail.

In this step, the hook 37 is moved forward until it penetrates the membrane 6, if present, and the wall 3a, drawing it towards the blade 35 of the knife 34 due to the effect of the spring 40.

The knife 34 is then rotated until the wall 3a is completely cut, the resected portion being held by the hook 37. The knife is then withdrawn and, if the operation is performed while blood is circulating in the vessel, the hole is closed by moving the membrane 6 as described previously.

Otherwise, if the operation is performed with interruption of the blood flow (possible thanks to the rapidity with which the device can be applied), the use of the shutter membrane is not necessary.

The sleeve 41 can now be withdrawn, freeing the segments 22 which open and make it possible to remove the applicator 21 from the device 20 fixed to the duct 3 (configuration in FIG. 7a).

With reference to FIGS. 16 to 23 the assembly is described of an end connector 50 to a duct or prosthesis 4 to be laterally connected to the duct 3 by means of the device 20.

According to the invention, the connector 50 comprises a first cylindrical body 51, preferably made from metal with a sloping end 53 and a stop collar 52 at the other end, and a second cylindrical body 54, preferably made from plastic, positioned over the first body and also equipped with a sloping end 56 and a collar 55 at the other end, designed to stop against the collar 52 of the body 51.

Application of a prosthesis 4 to the connector 50 also foresees the use of an instrument 58 (FIG. 21) consisting of:
- a cylindrical body 59 with a portion 65 whose outer diameter is slightly smaller than the inner diameter of the body 54 of the connector 50 and a second portion 66 with a smaller diameter and protruding from a sloping surface 60 of the body 59. The outer diameter of the second portion 66 corresponds to the diameter of the prosthesis 4 to be applied and is equipped with a crown of elastically expandable tabs 64;
- a double truncated cone-shaped nose-piece 61 protruding in front of the tabs and connected to a cylindrical return rod 67 sliding coaxially to the body 59 and operated from the outside by means of a manual screw 63 connected to the rod by internal threading.

When used, the body 54 of the connector 50 is first positioned on the body 59 of the instrument 58 (FIG. 20) and the body 51 is placed on the prosthesis 4, with an excess portion 69 previously cut longitudinally along a generatrix 68 corresponding to the centre line of the sloping end 53 of the body 51 (FIG. 16). The nose-piece 61 is then inserted in the prosthesis 4 and the tabs 64 are expanded by means of the return rod 62 so as to block the prosthesis and the body 51 in position (FIGS. 19, 22) and invert the portion 69 of the prosthesis 4 on the body 51 (FIG. 18). The body 54 is then slid forward, forcing it over the inverted portion 69 until it rests against the collars 52 and 55.

Figure 23:
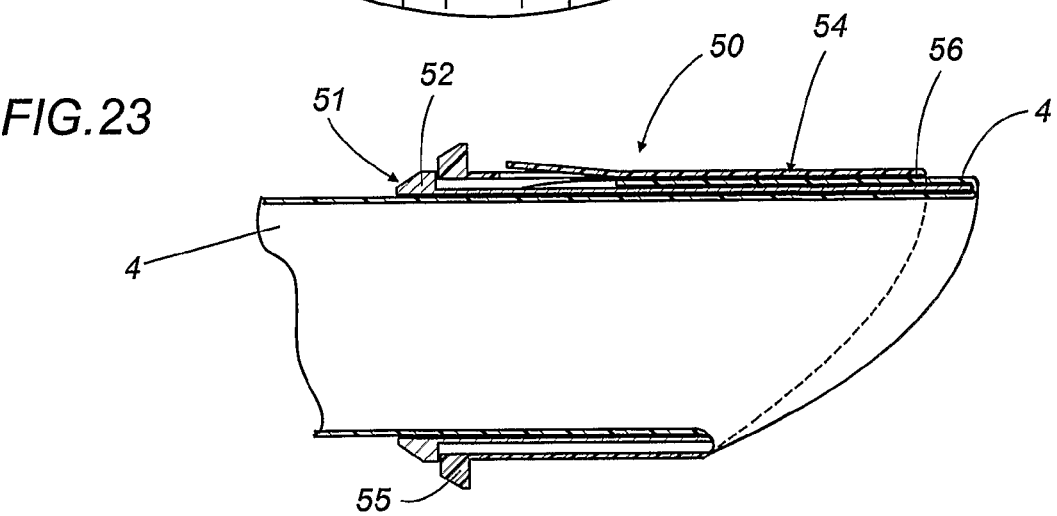
FIG. 23 shows a longitudinal cross-section of an end connector with a prosthesis applied.

In this configuration, the instrument 58 can be removed and the body 54 is clamped by interference on the prosthesis 4 and the prosthesis on the body 51 (FIGS. 17, 23).

Advantageously, the sloping end of the body 51 protrudes slightly with respect to the sloping end 56 of the body 54 in order to protect the edges of the duct wall at the level of the anastomosis hole and to prevent the blood flow from "opening" and widening the various layers forming the vessel wall which could even lead to occlusion of the vessel.

The end of the body 51 is also completely covered by the prosthesis 4 to prevent any contact, when in use, between the metal and the blood and the relative risks.

The length of the body 51 is also such that, once the end connector 50 has been inserted in the device 20, the sloping end 53 is substantially aligned with the inner span of the duct 3 to cover the edges of the anastomosis hole and at the same time to limit the diversion of the normal blood flow as much as possible.

With reference to FIG. 15 the end connector 50 is inserted in the device 20 until an elastic tab 57 on the body 54 snaps into a notch 70 present in the conduit 14 to prevent the connector 50 slipping out of the device 20.

Figure 8:
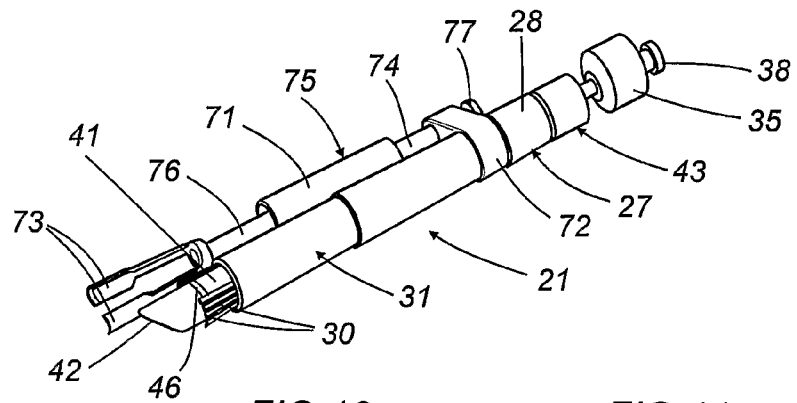
FIG. 8 is a prospective view of an applicator.
Figure 9:
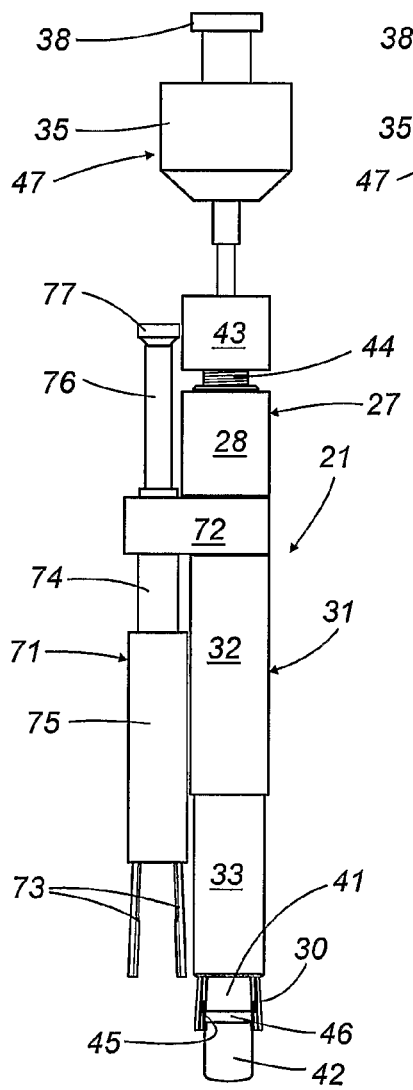
FIGS. 9-11 are respectively a view from above and the left side and right side of the applicator in FIG. 8.
Figure 10:
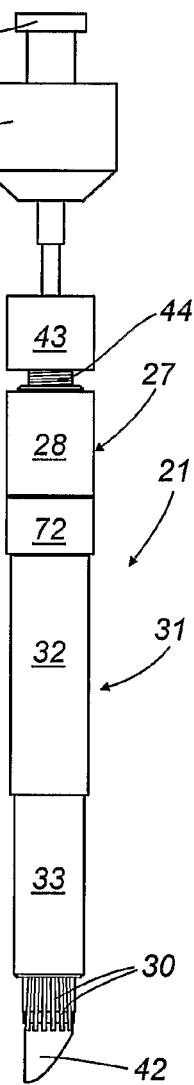
Figure 11:
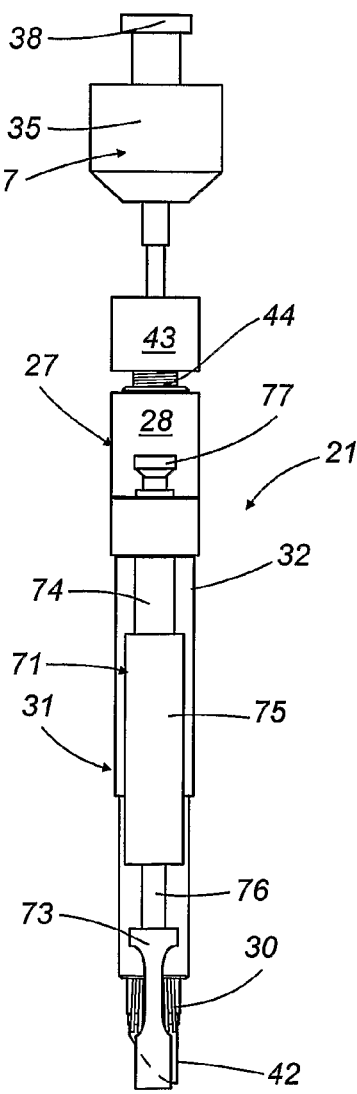

The connector 50 is preferably inserted in the device 20 by means of a gripping instrument 71 which can be coupled to the applicator 21 by a common connecting crosspiece 72 (FIG. 8).

With particular reference to FIGS. 6 and 7b, the instrument 71 comprises:
- a hollow cylindrical body 74 fixed to the crosspiece 72;
- a coaxial rod 76 which can slide inside the body 74 by operating a pushbutton 77, the rod being equipped with a pair of opposite and normally spread open elastic wings 73 protruding at the front;
- a cylindrical sleeve 75 that can slide axially over the wings 73 and force them to converge.

When in use, the wings 73 are normally spread open and it is possible to place a connector 50, with the prosthesis 4 mounted, between the wings 73 and then to move the sleeve 75 forward so as to close the collar 55 of the connector 50 between the ends of the wings 73. In this configuration, the sleeve 75, the wings 73 and the connector 50 move together by operating the rod 76. Advantageously, it is possible to fix a device 20 to the duct 3 with an applicator 21 that is already fitted with a connector 50 (FIG. 7b) with the rod 76 in the retracted position to facilitate the application of the device 20.

In this way, once the device 20 has been fixed to the duct 3 the rod 76 can be pushed forward so that the connector 50 protrudes with respect to the body of the applicator 21 (FIG. 6), and then insert the connector 50 in the device 20 until the tab 57 of the connector 50 snaps into the notch 70 of the device 20. It is then sufficient to withdraw the sleeve 75 to open the wings 73 and release the connector 50 (FIG. 15). It should be pointed out that the membrane 6, like the various components of the device and the connector, are preferably made from biocompatible material that can be perforated, for example polyurethane, silicone, PTFE, known material like Dacron®, and the like, since it will come into contact with body tissues and fluids.

Figure 24:
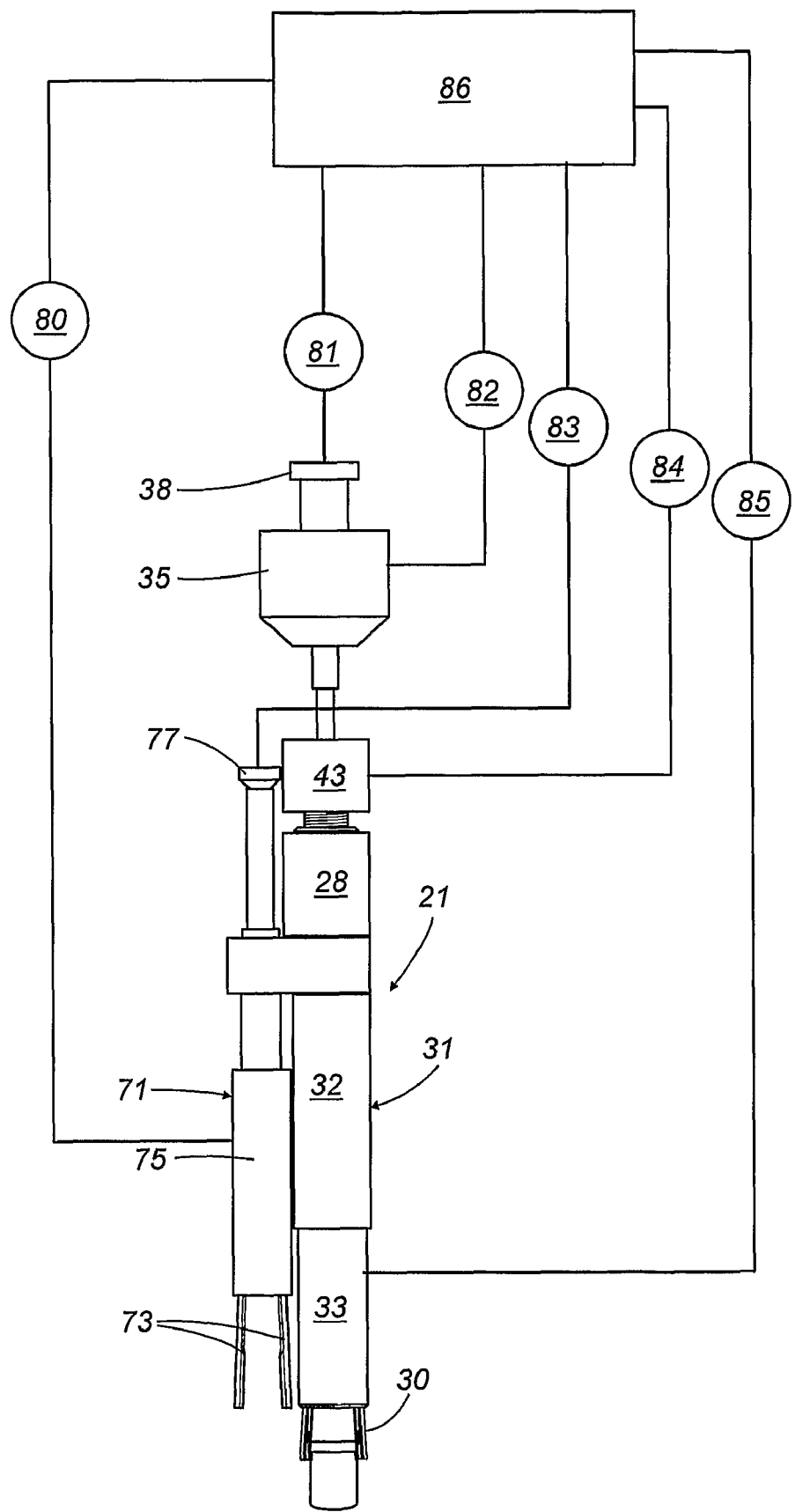
FIG. 24 shows a schematic view of the applicator in FIG. 9 with the relative motor drive of the moving parts.

FIG. 24 schematically shows an embodiment of the applicator device designed for automatic or semi automatic use.

In this embodiment, the movement of one or more of the linearly mobile parts, that is the pushbuttons 38 and 77 and the sliding sleeves 33 and 75, and/or the rotating parts, that is the knobs 35 are 43, can be driven by linear actuators (81, 83, 85, 80) and, respectively, rotation actuators (82, 84) connected to a control unit (86) to manage and control their movements.

Advantageously, the unit 86 can be connected to the motor drives 80-85 by cable or with a drive system without cables.

The invention achieves the proposed aims.

In fact, the hemorrhaging that occurs during the grafting operation is limited and controlled thanks to the presence of the membrane removably positioned between the coupling and the side wall of the duct to be anastomosed and made from flexible material that adapts to the irregularities of the duct or vessel wall.

In addition, the original continuity of the anastomosed vessel is maintained thanks to the coupling and in particular to the saddle-shaped portion and its opening.

The end-to-side anastomosis device described above can clearly be grafted in position quickly since it does not require sutures or particularly long procedures.

Finally, the end-to-side anastomosis device according to the invention can clearly be applied easily even by not highly qualified personnel, since the entire grafting procedure can be performed quite simply, thanks to the control of the blood flow by means of the membrane.

This invention also presents some advantages.

In fact, the end-to-side anastomosis device described above leaves the layers of the vessel in question unaltered, that is to say it does not cause relative sliding between the various layers thanks to the hooks and to their only partial perforation of the anastomosed duct. Moreover, the device according to the invention does not cause excessive injury to the anastomosed duct as the hooks of the fastener are the only invasive components and only partially penetrate the side wall of the duct.

Figure 5:
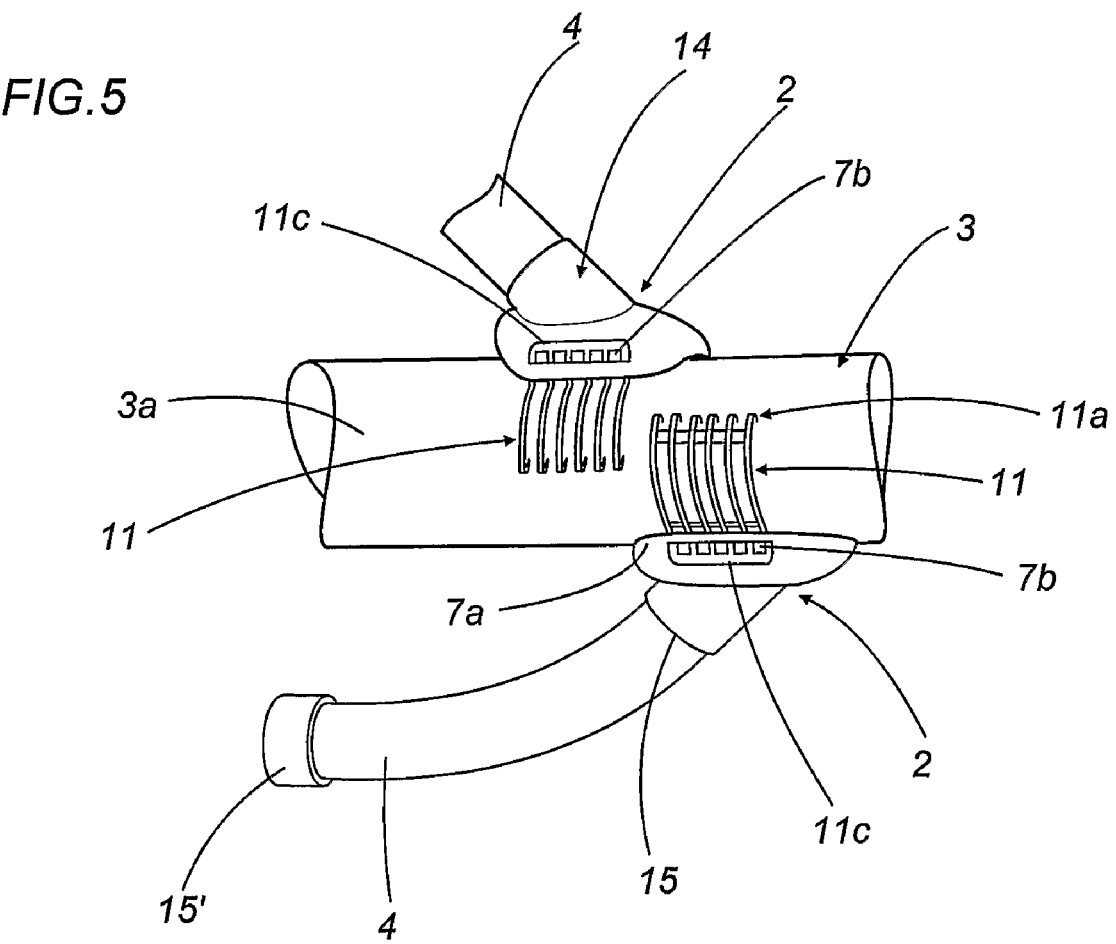
FIG. 5 is a prospective view of a working variation with the use of two (or more) devices as per FIG. 1.

Yet again, the end-to-side anastomosis device according to the invention allows a duct to be anastomosed even at points very close together without particular difficulties (see for example FIG. 5).

The invention offers a particular advantage in dialysis operations, in which it is possible to use two devices and one prosthesis connected to them to achieve the connection of arterial and venous circuits.

If it should be necessary to replace the prosthesis, it is in fact sufficient to close the membrane 6 (in this case, moving it like a shutter) avoiding all the complications of new operations, sutures, etc. as is usually the case.

In this regard it must be pointed out that an important feature of the device is that it is extremely easy to use and apply in various operating situations.

Thanks to the invention, it is therefore possible to implement new methods that have up to now been impossible or extremely risky.

For example, performing surgery with the device according to the intervention it is possible to bypass occlusions or aneurysms by connecting two or more devices with a prosthesis, applying them directly on the sections of the vessels concerned without interrupting the blood flow.

This avoids the need to foresee extracorporeal circulation or prolonged blood flow interruption.

Another advantage of the operating method consists of the possibility of using laparoscopy.

The invention described above is obviously appropriate for industrial application; it may also be modified and adapted in several ways without thereby departing from the scope of the inventive concept; all the details may also be replaced by technically equivalent elements.

The invention claimed is:

1. A device for end-to-side anastomosis of body ducts comprising:
a coupling (2) which can be positioned on a side wall (3a) of a first duct (3) and connectable to a second duct (4) in order to create a fluid communication between the first (3) and second duct (4), wherein said coupling (2) comprises a saddle-shaped portion (7) which can at least partially overlap the side wall (3a) of said first duct (3) and including an opening (8) to create a fluid communication between said first (3) and said second duct (4);
means of restraint (5) for attaching the coupling (2) to said first duct (3), wherein the means of restraint (5) act with a clamping movement for anchoring to the wall (3a), said means of restraint (5) comprising at least two elements (9, 10) that are elastically deformable so as to at least partially encircle said first duct (3) and to attach said coupling (2) to said first duct (3), wherein each elastically deformable element (9, 10) comprises a fastener (11) for attaching the coupling (2) to said first duct (3), each said fastener (11) comprising at least one hook (12) to only partially perforate the side wall (3a) of the first duct (3) and attach itself to the side wall (3a) of said first duct (3).

2. A device according to claim 1, further comprising at least one continuous membrane (6) slidingly positioned between said coupling (2) and the side wall (3a) of said first duct (3) and able to prevent on command the fluid communication between the first (3) and the second duct (4).

3. A device according to claim 2, in which said membrane (6) can be moved between at least one position in which it occludes said opening (8) in the saddle-shaped portion (7) and at least one position in which it creates a fluid communication between said opening (8) and said first duct (3).

4. A device according to claim 2, in which said membrane (6) is completely removable.

5. A device according to claim 2, in which said membrane (6) is made from material which can be perforated.

6. A device according to claim 2, in which said membrane (6) is made from biocompatible material.

7. A device according to claim 1, in which said hook (12) is positioned at one end (11a) of said fastener (11); the fastener (11) comprising a second end (11b), opposite the first (11a), attached, preferably removably, to said coupling (2).

8. A device according to claim 7, in which said second end (11b) of said fastener (11) is attached to the saddle-shaped portion (7) at the level of one peripheral edge (7a) of said saddle-shaped portion (7).

9. A device according to claim 1, in which said coupling (2) comprises a conduit (14) that extends around and away from said opening (8) in the saddle-shaped portion (7).

10. A device according to claim 9, in which said conduit (14) and a plane of said opening (8) form an angle between 30° and 90°, preferably 45°.

11. A device according to claim 9, in which said conduit (14) comprises a coupling portion (15) to connect said second duct (4) to the coupling (2).

12. A device according to claim 11, in which said coupling portion (15) and said second duct (4) are connected by mechanical interference.

13. A device according to claim 11, in which said coupling portion (15) and said second duct (4) are connected by snap-fit connection.

14. A device according to claim 11, in which said coupling portion (15) and said second duct (4) are connected by bayonet connection.

15. A device according to claim 9, in which said saddle-shaped portion (7) and said conduit (14) are made from biocompatible material.

16. A device according to claim 9, wherein said conduit (14) is prefitted with an end connector (15).

17. A device according to claim 1, in which said saddle-shaped portion (7) is made from flexible material to adapt to the curvature of the side wall (3a) of the first duct (3).

18. A device for end-to-side anastomosis of body ducts comprising:
- a coupling (2) which can be positioned on a side wall (3a) of a first duct (3) and connectable to a second duct (4) in order to create a fluid communication between the first (3) and second duct (4), wherein said coupling (2) comprises a saddle-shaped portion (7) which can at least partially overlap the side wall (3a) of said first duct (3);
- a conduit (14) connected to said saddle-shaped portion;
- means of restraint (5) for attaching the coupling (2) to said first duct (3), wherein the means of restraint (5) act with a clamping movement for anchoring to the side wall (3a), said means of restraint (5) comprising a series of hooks (22) positioned at two sides of the saddle-shaped portion (7), the hooks (22) being connected at one end to a ring (23) that is slidable on the conduit (14) and the hooks (22) passing through slots (24) in the saddle-shaped portion (7), terminating with curved ends (25), normally open and designed to grip the wall (3a) of the duct (3) in their closed configuration.

* * * * *